(12) United States Patent
Pak et al.

(10) Patent No.: US 11,384,059 B2
(45) Date of Patent: Jul. 12, 2022

(54) CARRIER, CATALYST, METHODS FOR PRODUCING THEM AND METHOD FOR PRODUCING ETHYLENE OXIDE

(71) Applicants: SCIENTIFIC DESIGN COMPANY, INC., Little Ferry, NJ (US); Noritake Co., Limited, Aichi (JP)

(72) Inventors: Serguei Pak, Teaneck, NJ (US); Yasuyuki Kato, Aichi (JP)

(73) Assignees: Scientific Design Company, Inc., Little Ferry, NJ (US); Noritake Co., Limited, Nagoya (JP)

( * ) Notice: Subject to any disclaimer, the term of this patent is extended or adjusted under 35 U.S.C. 154(b) by 0 days.

(21) Appl. No.: 16/225,147

(22) Filed: Dec. 19, 2018

(65) Prior Publication Data

US 2019/0127341 A1    May 2, 2019

Related U.S. Application Data

(62) Division of application No. 15/689,758, filed on Aug. 29, 2017.

(60) Provisional application No. 62/442,626, filed on Jan. 5, 2017.

(51) Int. Cl.

| C07D 301/10 | (2006.01) |
| B01J 23/66 | (2006.01) |
| B01J 21/08 | (2006.01) |
| B01J 23/50 | (2006.01) |
| B01J 23/58 | (2006.01) |
| B01J 23/68 | (2006.01) |
| B01J 21/12 | (2006.01) |

(52) U.S. Cl.
CPC ............ *C07D 301/10* (2013.01); *B01J 21/08* (2013.01); *B01J 23/50* (2013.01); *B01J 23/58* (2013.01); *B01J 23/66* (2013.01); *B01J 23/688* (2013.01); *B01J 21/12* (2013.01); *Y02P 20/52* (2015.11)

(58) Field of Classification Search
CPC ...................................................... B01J 21/04
USPC ................................. 502/355; 423/625, 628
See application file for complete search history.

(56) References Cited

U.S. PATENT DOCUMENTS

| 2,769,688 | A | * | 11/1956 | Koester | B01J 21/16 |
| | | | | | 423/132 |
| 2,774,744 | A | * | 12/1956 | Welling | C01F 7/20 |
| | | | | | 502/322 |
| 3,223,483 | A | * | 12/1965 | Osment | B01J 20/08 |
| | | | | | 423/131 |
| 4,631,267 | A | | 12/1986 | Lachman et al. | |
| 5,302,368 | A | * | 4/1994 | Harato | C01F 7/023 |
| | | | | | 423/111 |
| 9,006,127 | B2 | | 4/2015 | Jiang et al. | |
| 9,067,198 | B2 | | 6/2015 | Pak | |
| 9,387,459 | B2 | † | 7/2016 | Heinl | |
| 2005/0096219 | A1 | | 5/2005 | Szymanski et al. | |
| 2007/0037704 | A1 | | 2/2007 | Rizkalla | |
| 2007/0037991 | A1 | * | 2/2007 | Rizkalla | B01J 21/04 |
| | | | | | 549/533 |
| 2010/0150820 | A1 | * | 6/2010 | Kanazirev | C01F 7/021 |
| | | | | | 423/626 |
| 2011/0301368 | A1 | * | 12/2011 | Pak | C07D 301/08 |
| | | | | | 549/536 |
| 2012/0226058 | A1 | * | 9/2012 | Pak | B01J 23/688 |
| | | | | | 549/536 |
| 2014/0221196 | A1 | * | 8/2014 | Suchanek | B01J 37/0018 |
| | | | | | 502/202 |

FOREIGN PATENT DOCUMENTS

| JP | 57 171435 | * | 10/1982 | ............. B01J 21/12 |
| JP | 2015-199059 | * | 11/2015 | ............. B01J 23/68 |
| JP | 2015-199059 A | | 11/2015 | |
| JP | 2015-199060 | * | 11/2015 | |
| JP | 2015-199060 A | | 11/2015 | |
| TW | 201534393 A | | 9/2015 | |
| TW | 201700438 A | | 1/2017 | |
| WO | 2016/196709 A1 | | 12/2016 | |
| WO | 2016/196710 A1 | | 12/2018 | |

OTHER PUBLICATIONS https://www.nikkeikin.com/pdf/products/chemical/low_soda_alumina.pdf (Year: NA).*
https://www.sumitomo-chem.co.jp/english/products/files/docs/en_a06003.pdf (Year: NA).*
https://www.sdk.co.jp/assets/files/ceramics%20%20filler/filler%20english.pdf (Year: NA).*
Concise Description of the Relevance of U.S. Pat. No. 9,387,459 with Respect to U.S. Appl. No. 16/225,147, dated Oct. 17, 2019.
Extended European Search Report issued in EP 17890223.5 dated Aug. 12, 2020, 6 pages.
Notice of Grounds for Rejection received in Japanese Patent application No. 2019-536501, dated Nov. 4, 2020, 7 pages.
Decision of Refusal received in Japanese Patent application No. 2019-536501, dated Jun. 29, 2021, 7 pages.
Examination Report dated Sep. 29, 2019 received in Cooperation Council for the Arab States of the Gulf Patent GC 2017-34043.
Office Action dated Nov. 23, 2021 received in U.S. Patent Application Serial No. 15/689,758, 22 pages.

\* cited by examiner
† cited by third party

*Primary Examiner* — Patricia L. Hailey

(74) *Attorney, Agent, or Firm* — Scully, Scott, Murphy & Presser, P.C.

(57) ABSTRACT

A carrier for an ethylene epoxidation catalyst, the carrier comprising a porous alumina body formed of sintered particles of alumina in a substantial absence of inorganic binder species other than alumina, wherein the substantial absence of inorganic binder species corresponds to an amount of less than 0.6 wt % inorganic binder species other than alumina and comprises at least a substantial absence of silicon-containing species.

9 Claims, No Drawings

CARRIER, CATALYST, METHODS FOR PRODUCING THEM AND METHOD FOR PRODUCING ETHYLENE OXIDE

RELATED APPLICATIONS

The present application is a divisional application of U.S. application Ser. No. 15/689,758, filed Aug. 29, 2017, which claims the benefit of U.S. Provisional Application Ser. No. 62/442,626, filed Jan. 5, 2017, the entire contents of which are incorporated herein by reference. The present application asserts priority to the Jan. 5, 2017 filing date of the foregoing provisional application.

FIELD OF THE INVENTION

The present disclosure relates to a carrier, a catalyst, methods for producing them and a method for producing ethylene oxide.

BACKGROUND

Alumina is well known to be useful as a catalyst support (carrier) in silver-based catalysts used in the epoxidation of olefins (see, e.g., U.S. Pat. No. 6,815,395). Support materials are generally prepared by fusing high purity aluminum oxide along with a permanent inorganic binder, typically a silicon-containing material, such as silica. For example, the carrier may include 90 percent or more by weight of alpha alumina and up to 6 percent by weight of silica. The resulting carriers are generally very porous and have a high surface area.

In known processes of making a support, alumina particles formed of alpha alumina and/or transition alumina (alpha alumina precursors) are thoroughly mixed with a volatile organic binder and a permanent inorganic binder. The volatile organic binder holds together the components of the alumina particles during its processing. The permanent inorganic binder has a melting temperature below that of the alumina particles and induces fused bonding at points of contact between alumina particles. The permanent inorganic binder imparts mechanical strength to the finished carrier and generally functions in a non-promoting capacity. After thorough dry-mixing, sufficient water is added to the mass to form the mass into a paste-like extrudable admixture. Particles are then formed from the paste by any of the known means, such as high pressure extrusion, tableting, granulation or other ceramic forming processes. Next, by drying the particles, and then sintering at a high temperature, the preparation of the carrier, which includes a porous alumina body composed of sintered particles of alumina, is completed. In the firing step, the volatile organic binders are generally decomposed and volatilized to carbon dioxide and water.

There has long been an effort to improve the activity, selectivity, and stability of ethylene epoxidation catalysts. Most of these efforts have sought to achieve an improved catalyst by, for example, careful selection of promoting species, amount of silver, carrier surface area, carrier pore size distribution, and conditions (e.g., temperature, precursor and additive concentrations, etc) under which the ethylene epoxidation process is conducted. However, these above conventional approaches have yielded only limited additional improvements. Therefore, there would be a benefit in a new approach, particularly one that can be readily integrated into existing process designs and that is facile and cost effective.

Accordingly, an important purpose of the present invention is to provide a carrier, a catalyst, methods for producing them, and a method for producing ethylene oxide that can be easily incorporated into the existing process design and is facile and cost-effective, while improving activity, selectivity and stability of the ethylene epoxidation catalyst,

SUMMARY

The present disclosure is foremost directed to a carrier (i.e., support) for an ethylene epoxidation catalyst. The carrier is a porous alumina body formed of sintered particles of alumina in a substantial or complete absence of at least silicon-containing species. Particularly since most of the inorganic binder species are silicon-based, the substantial or complete absence of silicon-containing species amounts to a substantial or complete absence of most inorganic binder species. However, in some embodiments, the carrier contains a substantial or complete absence of all inorganic binder species, whether silicon-based or not.

The carrier described above has herein been found useful for producing an ethylene epoxidation catalyst having an improved catalyst activity, selectivity, and/or stability. The carrier advantageously achieves this improvement by means other than by promoting species, amount of silver, carrier surface area, carrier pore size distribution, and conditions under which the ethylene epoxidation process is conducted, as conventionally practiced in the art. Moreover, the carrier and process for its production can be readily integrated into existing process designs in a facile and cost effective manner.

The instant disclosure is also directed to a method for preparing the carrier described above. The method includes: a) preparing a composition containing alumina particles, water, and a sacrificial organic binder, in the substantial absence of an inorganic component other than alumina; b) molding the composition into a structure; c) heating the structure for a sufficient time and at a sufficient temperature to volatilize the sacrificial organic binder and form a porous structure; and d) sintering the porous structure at a temperature of 1000° C. or above for a sufficient time to produce the porous alumina body formed of sintered particles of alumina in a substantial absence of inorganic binder species other than alumina that function in a non-promoting capacity in the catalyst; wherein the substantial absence of inorganic binder species includes at least a substantial absence of silicon-containing species.

The instant disclosure is also directed to an ethylene epoxidation catalyst that includes the above-described carrier and a catalytic amount of silver supported on surfaces of the carrier. A method for producing the catalyst is also herein described. The method involves depositing a catalytically effective amount of silver supported onto surfaces of the carrier described above.

The instant disclosure is also directed to a method for the vapor phase conversion (i.e., oxidation, epoxidation) of ethylene to ethylene oxide (EO) in the presence of oxygen. The method includes reacting a reaction mixture of at least ethylene and oxygen in the presence of the ethylene epoxidation catalyst described above, which contains the specially prepared carrier described above.

A first particular aspect of the present disclosure is directed to a carrier for an ethylene epoxidation catalyst comprising a porous alumina body formed of sintered particles of alumina in a substantial absence of inorganic binder species other than alumina, wherein the substantial absence of inorganic binder species corresponds to an amount of less than 0.6 wt % (by weight of the carrier) of inorganic binder species other than alumina and comprises at least a substantial absence (i.e., an amount of less than 0.6 wt %) of silicon-containing species.

A second particular aspect of the present disclosure is directed to an ethylene epoxidation catalyst comprising a) a carrier comprising a porous alumina body formed of sintered particles of alumina in a substantial absence of inorganic binder species other than alumina, wherein the substantial absence of inorganic binder species corresponds to an amount of less than 0.6 wt % (by weight of the carrier) of inorganic binder species other than alumina and comprises at least a substantial absence (i.e., an amount of less than 0.6 wt %) of silicon-containing species; and b) a catalytic amount of silver on surfaces of the carrier.

A third particular aspect of the present disclosure is directed to a method for producing a carrier for an ethylene epoxidation catalyst in which the carrier comprises a porous alumina body formed of sintered particles of alumina in a substantial absence of inorganic binder species other than alumina, wherein the method comprises: a) preparing a composition comprising alumina particles, water, and a volatile organic binder, in the substantial absence of inorganic binder species other than alumina; b) molding the composition into a structure; c) heating the structure in such a way as to volatilize the volatile organic binder and form a porous structure; and d) sintering the porous structure at a temperature of 1000° C. or above in such a way as to produce the porous alumina body formed of sintered particles of alumina in a substantial absence of inorganic binder species other than alumina; wherein the substantial absence of inorganic binder species corresponds to an amount of less than 0.6 wt % (by weight of the carrier) of inorganic binder species other than alumina and comprises at least a substantial absence (i.e., an amount of less than 0.6 wt %) of silicon-containing species.

A fourth particular aspect of the present disclosure is directed to a method for producing a catalyst effective in the oxidative conversion of ethylene to ethylene oxide, wherein the method comprises: (i) providing a carrier comprising a porous alumina body formed of sintered particles of alumina in a substantial absence of inorganic binder species other than alumina, wherein the substantial absence of inorganic binder species corresponds to an amount of less than 0.6 wt % (by weight of the carrier) of inorganic binder species other than alumina and comprises at least a substantial absence (i.e., an amount of less than 0.6 wt %) of silicon-containing species; and (ii) depositing a catalytically effective amount of silver onto surfaces of the carrier.

A fifth particular aspect of the present disclosure is directed to a method for producing ethylene oxide for the vapor phase conversion of ethylene to ethylene oxide in the presence of oxygen, wherein the method comprises reacting a reaction mixture comprising ethylene and oxygen in the presence of a catalyst comprising: a) a carrier comprising a porous alumina body formed of sintered particles of alumina in a substantial absence of inorganic hinder species other than alumina, wherein the substantial absence of inorganic binder species corresponds to an amount of less than 0.6 wt % (by weight of the carrier) of inorganic binder species other than alumina and comprises at least a substantial absence (i.e., an amount of less than 0.6 wt %) of silicon-containing species; and b) a catalytic amount of silver on surfaces of the carrier.

DETAILED DESCRIPTION

In one aspect, the present disclosure is directed to a carrier (i.e., support) for an ethylene epoxidation catalyst. The carrier is a porous alumina body formed of sintered particles of alumina in a substantial absence of inorganic binder species other than alumina. The porous alumina body binds particles together by sintering of alumina, and is in a state in which pores are left in the interior, while having a strength (for example, more than 60N in crushing strength by Kiya type digital hardness tester) necessary for the carrier. The alumina particles are preferably composed of any of the refractory alumina compositions known in the art for use in ethylene oxidation catalysts. Preferably, the alumina is alpha-alumina. The alpha-alumina used in the inventive carrier preferably has a very high purity, i.e., about 95% or more, and more preferably, 98 wt. %, 99 wt. %, or more alpha-alumina. In some embodiments, the alpha-alumina is a low alkali metal alumina or a low alkali metal reactive alumina. The term "reactive alumina" as used herein generally indicates an alpha-alumina with good sinterability and having a particle size that is very fine, i.e., generally, when observed by a scanning electron microscope (SEM), of 2 microns or less. A "low alkali metal alumina" can indicate an alumina material having alkali metal-containing species. Good sinterability is generally derived from a 2-micron or less particle size.

The term "inorganic binder species," is herein understood to refer to any of the inorganic species conventionally used in the art as permanent binders, particularly those inorganic species containing silicon. Permanent binders are generally included in the conventional art during carrier preparation and retained in the carrier in order to ensure adequate bonding of alumina particles. Without such permanent binders, the alumina body would not be expected to retain a shape and be prone to disintegration into its constitute particles. The invention described herein significantly departs from the conventional art by substantially omitting inorganic binder species while still providing a robust carrier that maintains its shape and is not prone to disintegration. The invention achieves this by relying on particle-particle fusing in place of inorganic binders. Generally, the inorganic binder species do not function as promoters in the resulting catalyst after catalytic metal component (for example, silver) deposition. However, in the event that an inorganic binder species also possesses a promoting ability, the inorganic binder species is still substantially excluded from the carrier.

The term "substantial absence of inorganic binder species" provides that at least all silicon-containing species are substantially absent from the carrier. Some examples of silicon-containing species, generally used as permanent binders and excluded herein, include inorganic clay or clay-type materials (e.g., kaolinite), silica, silicates (e.g., of elements of Groups I and II of the Periodic Table of the Elements, such as sodium silicate, calcium silicate, magnesium silicate, and talc), silica sol, feldspar, silicon nitride, silicon carbide, diatomaceous earth, zeolites, and the general class of aluminosilicates, such as mullite. Non-silicon inorganic binder species may also be substantially excluded. Some examples of non-silicon inorganic binder species excluded from the carrier include, for example, alkali metal oxides, alkaline earth metal oxides, titanium oxide, and zirconium oxide. In some embodiments, any oxide material other than aluminum oxide may be substantially absent from the carrier.

Significantly, any of the compositions provided above as exemplary of inorganic binder species could be present in the carrier if the inorganic species is not functioning to bind alumina particles. To function as a binder, the inorganic species must function, to at least some degree, by holding together (i.e., binding) particles of alumina. If the inorganic species is not fulfilling a binding function (for example, by only coating surfaces of the alumina particles after the alumina particles have been fused), then the inorganic species are permitted in the carrier. The inorganic species that could be present in the carrier in a non-binding capacity could function, for example, as a promoting species, as further described below. Generally, the carrier itself, before being converted to a catalyst by deposition of silver, does not possess promoting species. Thus, in a typical embodiment for the present purposes, the carrier, before being converted to a catalyst, is constructed solely of sintered particles of alumina.

The term "substantial absence," as used herein, generally refers to an amount of less than 0.6 wt % of inorganic binder species (or silicon-containing species, in particular) by weight of the carrier. In different embodiments, the inorganic binder species is in an amount of up to or less than 0.5 wt %, 0.4 wt %, 0.3 wt %, 0.2 wt %, 0.1 wt %, 0.05 wt %, 0.04 wt %, 0.03 wt %, 0.02 wt %, 0.01 wt %, 0.005 wt %, or 0.001 wt % by weight of the carrier. In other embodiments, the amount of inorganic binder species, or silicon-containing species in particular, is completely absent or undetectable, i.e., an amount of 0 wt %.

The alumina particles in the carrier can have any of the particle sizes known in the art, and are typically microparticles. In different embodiments, the carrier microparticles can have a particle size (i.e., diameter, if substantially spherical) of precisely, about, at least, greater than, up to, or less than, for example, 1, 2, 3, 4, 5, 6, 7, 8, 9, 10, 12, 15, or 20 microns, or the carrier microparticles may have a size within a range bounded by any two of the foregoing exemplary values. The carrier precursor particles may also be composed of two or more portions of microparticles of different sizes or size ranges, typically selected from the above exemplary sizes. Moreover, each portion of the carrier precursor particles may be in a suitable weight percentage by total weight of carrier precursor or finished carrier (before silver impregnation). In different embodiments, one or more portions of carrier microparticles in different size ranges may be present in an amount of precisely, about, at least, greater than, up to, or less than, for example, 1 wt %, 2 wt %, 5 wt %, 20 wt %, 25 wt %, 30 wt %, 40 wt %, 50 wt %, 60 wt %, 70 wt %, 80 wt %, 90 wt %, 95 wt %, 98 wt %, or 99 wt %, or within a weight percentage (wt %) range bounded by any of the foregoing values.

The carrier can have any suitable distribution of pore diameters. As used herein, the term "pore diameter" is used interchangeably with the term "pore size", The pore volume (and pore size distribution) described herein can be measured by any suitable method, but are more preferably obtained by the conventional mercury porosimeter method as described in, for example. Drake and Ritter, *Ind. Eng Chem. Anal. Ed.*, 787 (1945).

Typically, the pore diameters are at least about 0.01 microns (0.01 µm), and more typically, at least about 0.1 µm. Typically, the pore diameters are no more than or are less than about 10, 15, 20, 25, 30, 35, 40, 45, or 50 µm. In different embodiments, the pore diameters are about, at least, above, up to, or less than, for example, 0.5 µm, 1.0 µm, 1.5 µm, 2 µm, 3 µm, 5 µm, 7 µm, 8 µm, 9 µm, 10 µm, 12 µm, 15 µm, 18 µm, or 20 µm, or the pore diameters are within a range bounded by any two of the foregoing exemplary values. Any range of pore sizes, as particularly derived from any of the above exemplary values, may also contribute any suitable percentage of the total pore volume, such as at least, greater than, up to, or less than, for example, 1, 5, 10, 15, 20, 25, 30, 40, 50, 60, 70, 80, 90, 95, or 98% of the total pore volume. In some embodiments, a range of pore sizes may provide the total (i.e., 100%) pore volume.

The carrier may possess a pore size distribution (e.g., within a range as set forth above) characterized by the presence of one or more pore sizes of peak concentration, i.e., one or more maxima (where the slope is approximately zero) in a pore size vs. pore volume distribution plot. A pore size of maximum concentration is also referred to herein as a peak pore size, peak pore volume, or peak pore concentration. Furthermore, each pore size distribution can be characterized by a single mean pore size (mean pore diameter) value. Accordingly, a mean pore size value given for a pore size distribution necessarily corresponds to a range of pore sizes that results in the indicated mean pore size value. Any of the exemplary pore sizes provided above can alternatively be understood to indicate a mean (i.e., average or weighted average) or median pore size in a pore size distribution. Any of the exemplary pore sizes provided above may also be interpreted to be the lower and upper bounds of a peak in a pore volume distribution plot.

In some embodiments, the carrier possesses a multimodal pore size distribution within any of the pore size ranges described above. The multimodal pore size distribution can be, for example, bimodal, trimodal, or of a higher modality. The multimodal pore size distribution is characterized by the presence of different pore sizes of peak concentration (i.e., different peak pore sizes) in a pore size vs. pore volume distribution plot. The different peak pore sizes are preferably within the range of pore sizes given above. Each peak pore size can be considered to be within its own pore size distribution (mode), i.e., where the pore size concentration on each side of the distribution falls to approximately zero (in actuality or theoretically). In one embodiment, different pore size distributions, each having a peak pore size, are non-overlapping by being separated by a volume concentration of pores of approximately zero (i.e., at baseline). In another embodiment, different pore size distributions, each having a peak pore size, are overlapping by not being separated by a volume concentration of pores of approximately zero. Each mode of pores may contribute any suitable percentage of the total pore volume, such as any of the percentages or ranges thereof, provided above.

The macroscale shape and morphology of the carrier, i.e., after compounding and calcining of the carrier particles, can be any of the numerous shapes and morphologies known in the art. For example, the carrier can be in the form of macroparticles, chunks, pellets, rings, spheres, three-holes, wagon wheels, cross-partitioned hollow cylinders, and the like, of a size preferably suitable for employment in fixed-bed epoxidation reactors.

The carrier of the invention typically has a B.E.T. surface area of up to 20 $m^2/g$. The B.E.T. surface area is more typically in the range of about 0.1 to 10 m"/g, and more typically from 1 to 5 $m^2/g$. In other embodiments, the carriers of the invention are characterized by having a B.E.T. surface area from about 0.3 $m^2/g$ to about 3 $m^2/g$, or from about 0.6 $m^2/g$ to about 2.5 $m^2/g$, or from about 0.7 $m^2/g$ to about 2.0 $m^2/g$. The B.E.T. surface area described herein can be measured by any suitable method, but is more preferably obtained by the method described in Brunauer, S., et al., *J. Am. Chem. Soc.*, 60, 309-16 (1938). The final support typically possesses a water absorption value (water pore volume) ranging from about 0.1 cc/g to about 0.8 cc/g, more typically about 0.2 cc/g to about 0.8 cc/g, and more typically from about 0.25 cc/g to about 0.6 cc/g.

In another aspect, the present disclosure is directed to a method for producing the carrier described above. The method employs many of the conventional techniques well known in the art, but with the significant modification that a permanent inorganic binder, as described above, is not added to the precursor mixture before sintering or calcining. In the method, the carrier may be produced by, for example, combining alumina microparticles, a solvent (e.g., water), a temporary binder or burnout material (i.e., sacrificial organic binder), and/or a porosity controlling agent, and then shaping, molding, and/or extruding the resulting paste into a structure, before sintering or calcining the preform. The conventional carrier preparation process is described in, for example, U.S. Pat. No. 8,791,280, the contents of which are herein incorporated by reference. If any of the above components in the carrier preform also functions as a permanent inorganic binder, it should not be included in the preform. If trace amounts of inorganic binder species (particularly silicon-containing species) are included in any of the components in the carrier preform, the inorganic binder species should not exceed the lower limit in the final carrier, as provided above, i.e., should result in less than 0.6 wt % inorganic binder species by weight of the final produced carrier.

Temporary binders, or burnout materials, include cellulose, substituted cellulases, e.g., methylcellulose, ethylcellulose, and carboxyethylcellulose, stearates (such as organic stearate esters, e.g., methyl or ethyl stearate), waxes, granulated polyolefins (e.g., polyethylene and polypropylene), walnut shell flour, and the like, which are decomposable at the temperatures employed. Besides functioning as temporary binders, the temporary binders also impart porosity to the carrier material during sintering. Burnout material is used primarily to ensure the preservation of a porous structure during the green (i.e., unsintered phase) in which the mixture may be shaped by molding or extrusion processes. Burnout materials are substantially or completely removed by thermal decomposition during the firing stage to produce the finished carrier.

The formed paste is extruded or molded into the desired shape and sintered at a temperature (sintering temperature) typically of at least or 1000° C. to 1650° C. (1000° C. or more and 1650° C. or less) to form the carrier. In different embodiments, the formed paste is fired at a temperature of about 1050° C., 1100° C., 1150° C., 1200° C., 1250° C., 1300° C., 1350° C., 1400° C., 1450° C., 1500° C., 1525° C., 1530° C., 1550° C., 1575° C., 1590° C., 1600° C. or 1650° C., or at a temperature within a range bounded by any two of the foregoing values, wherein the term "about," as used herein, generally indicates no more than +2% or ±1% of an indicated value (i.e., "about 1200° C." can generally encompass 1180° C. to 1220° C. in its broadest sense). In embodiments in which the particles are formed by extrusion, it may be desirable to include conventional extrusion aids. In some embodiments, the performance of the carrier is enhanced if it is treated by soaking the carrier in a solution of an alkali hydroxide, such as sodium hydroxide, potassium hydroxide, or an acid such as $HNO_3$ as described in U.S. Pat. No. 7,507,844, the contents of which are herein incorporated by reference. After treatment, the carrier is preferably washed, such as with water, to remove unreacted dissolved material and treating solution, and then optionally dried. The foregoing soaking treatment may also serve to further or completely remove any residue of inorganic binder species, or more specifically, any residue of silicon-containing species. Here, the sintering temperature means a temperature in atmosphere at a vicinity of a carrier at the time of sintering.

The time for holding at the sintering temperature (i.e., sintering time) can be for example, 10 minutes or more and 10 hours or less, preferably 30 minutes or more and 5 hours or less, more preferably 45 minutes or more and 3 hours or less.

In another aspect, the present disclosure is directed to an ethylene epoxidation catalyst in which the above-described carrier is incorporated. The catalyst includes at least the alumina carrier described above along with a catalytically effective amount of silver on surfaces of the carrier. The term "surfaces," as used herein, refers to both the outer surface of the carrier as well as internal pore surfaces of the carrier. The amount of silver on the carrier can be any of the amounts conventionally used in the art, typically 15-40 wt %.

The silver catalyst may or may not also include one or more promoting species. As used herein, a "promoting amount" of a certain component of a catalyst refers to an amount of that component that works effectively to provide an improvement in one or more of the catalytic properties of the catalyst when compared to a catalyst not containing said component. Examples of catalytic properties include, inter alia, operability (resistance to runaway), selectivity, activity, conversion, stability and yield. It is understood by one skilled in the art that one or more of the individual catalytic properties may be enhanced by the "promoting amount" while other catalytic properties may or may not be enhanced or may even be diminished. It is further understood that different catalytic properties may be enhanced at different operating conditions. For example, a catalyst having enhanced selectivity at one set of operating conditions may be operated at a different set of conditions wherein the improvement is exhibited in the activity rather than in the selectivity.

In a first embodiment, the catalyst includes a promoting amount of an alkali metal or a mixture of two or more alkali metals. Suitable alkali metal promoters include, for example, oxides or non-oxide salts of lithium, sodium, potassium, rubidium, cesium or combinations thereof. Cesium is often preferred, with combinations of cesium with other alkali metals also being preferred. The amount of alkali metal will typically range from about 10 ppm to about 3000 ppm, more typically from about 15 ppm to about 2000 ppm, more typically from about 20 ppm to about 1500 ppm, and even more typically from about 50 ppm to about 1000 ppm by weight of the total catalyst, expressed in terms of the alkali metal. In some embodiments, alkali metal species in oxide or non-oxide salt form (or all alkali metal species) are substantially or completely excluded from the catalyst or carrier, e.g., an amount of up to or less than 1, 0.5, or 0.1 ppm by weight of the catalyst or carrier.

In a second embodiment, the catalyst includes a promoting amount of an alkaline earth metal or a mixture of two or more alkaline earth metals. Suitable alkaline earth metal promoters include, for example, oxides or non-oxide salts of beryllium, magnesium, calcium, strontium, and barium or combinations thereof. The amounts of alkaline earth metal promoters are used in similar amounts as the alkali metal promoters described above. In some embodiments, alkaline earth metal species in oxide or non-oxide salt form (or all alkaline earth metal species) are substantially or completely excluded from the catalyst or carrier, e.g., an amount of up to or less than 1, 0.5, or 0.1 ppm by weight of the catalyst or carrier.

In a third embodiment, the catalyst includes a promoting amount of a main group element or a mixture of two or more main group elements other than elements of Group 14 (carbon group). Suitable main group elements include, for example, oxides, non-oxide salts, or elemental forms of any of the elements of Group 13 (e.g., boron, aluminum, gallium, and indium), Group 15 (e.g., nitrogen, phosphorus, arsenic, and antimony), Group 16 (e.g., sulfur, selenium, and tellurium), and Group 17 (halogens) of the Periodic Table of the Elements. In some embodiments, the catalyst can include a promoting amount of one or more sulfur compounds, one or more phosphorus compounds, one or more boron compounds, one or more halogen-containing compounds, or combinations thereof. In some embodiments, main group metal species in oxide, non-oxide salt form, or elemental form are substantially or completely excluded from the catalyst or carrier, e.g., an amount of up to or less than 1, 0.5, or 0.1 ppm by weight of the catalyst or carrier.

In a fourth embodiment, the catalyst includes a promoting amount of a transition metal or a mixture of two or more transition metals. Suitable transition metals include, for example, oxides, non-oxide salts, or elemental forms of the elements of Group 3 (scandium group), Group 4 (titanium group), Group 5 (vanadium group), Group 6 (chromium group), Group 7 (manganese group), Group 8 (iron, cobalt, nickel groups), Group 9 (copper group), and Group 10 (zinc group) of the Periodic Table of the Elements, as well as combinations thereof. More typically, the transition metal is an early transition metal, i.e., from Groups 3-6, such as, for example, hafnium, yttrium, molybdenum, tungsten, rhenium, chromium, titanium, zirconium, vanadium, tantalum, niobium, or a combination thereof. The transition metal promoters are typically present in an amount of from about 0.1 micromoles per gram to about 10 micromoles per gram, more typically from about 0.2 micromoles per gram to about 5 micromoles per gram, and even more typically from about 0.5 micromoles per gram to about 4 micromoles per gram of total catalyst, expressed in terms of the metal. In some embodiments, transition metal species in oxide, non-oxide salt form, or elemental form are substantially or completely excluded from the catalyst or carrier, e.g., an amount of less than 0.1, 0.05, or 0.01 micromoles per gram by weight of the catalyst or carrier.

The catalyst may also include a promoting amount of a rare earth metal or a mixture of two or more rare earth metals. The rare earth metals include oxides or non-oxide salts of any of the elements having an atomic number of 57-103. Some examples of these elements include lanthanum (La), cerium (Ce), and samarium (Sm). The rare earth species is typically included in similar amounts as the transition metal species. In some embodiments, oxide or non-oxide salts of rare earth metal species are substantially or completely excluded from the catalyst or carrier.

Of the promoters listed, rhenium (Re) can be included as a particularly efficacious promoter for ethylene epoxidation high selectivity catalysts. The rhenium component in the catalyst can be in any suitable form, but is more typically one or more rhenium-containing compounds (e.g., a rhenium oxide) or complexes. The rhenium can be present in an amount of, for example, about 0.001 wt. % to about 1 wt. %. More typically, the rhenium is present in amounts of, for example, about 0.005 wt. % to about 0.5 wt. %, and even more typically, from about 0.01 wt. % to about 0.05 wt. % based on the weight of the total catalyst including the support, expressed as rhenium metal. In some embodiments, rhenium is not included in the catalyst.

In another aspect, the invention is directed to a process for producing the ethylene epoxidation catalyst produced described above. In order to produce the catalyst, a carrier having the above-described characteristics is first provided with a catalytically effective amount of silver by impregnating the carrier with a silver impregnation solution. The carrier can be impregnated with silver and any desired promoters by any of the conventional methods known in the art, e.g., by excess solution impregnation immersion), incipient wetness impregnation, spray coating, and the like. Typically, the carrier material is placed in contact with the silver-containing solution until a sufficient amount of the solution is absorbed by the carrier. In this way, silver and any desired promoters are deposited on surfaces located in outer (i.e., exterior) and inner (i.e., interior) regions of the carrier. In some embodiments, the quantity of the silver-containing solution used to impregnate the carrier is no more than is necessary to fill the pore volume of the carrier. Infusion of the silver-containing solution into the carrier can be aided by application of a vacuum. A single impregnation or a series of impregnations, with or without intermediate drying, may be used, depending in part on the concentration of the silver component in the solution. Impregnation procedures are described in, for example, U.S. Pat. Nos. 4,761,394, 4,766,105, 4,908,343, 5,057,481, 5,187,140, 5,102,848, 5,011,807, 5,099,041 and 5,407,888, all of which are incorporated herein by reference. Known procedures for pre-deposition, co-deposition, and post-deposition of the various promoters can also be employed.

Silver compounds useful for impregnation include, for example, silver oxalate, silver nitrate, silver oxide, silver carbonate, a silver carboxylate, silver citrate, silver phthalate, silver lactate, silver propionate, silver butyrate and higher fatty acid salts and combinations thereof. The silver solution used to impregnate the carrier can contain any suitable solvent. The solvent can be, for example, water-based, organic-based, or a combination thereof. The solvent can have any suitable degree of polarity, including highly polar, moderately polar or non-polar, or substantially or completely non-polar. The solvent typically has sufficient solvating power to solubilize the solution components. Some examples of water-based solvents include water and water-alcohol mixtures. Some examples of organic-based solvents include, but are not limited to, alcohols (e.g., alkanols), glycols (e.g., alkyl glycols), ketones, aldehydes, amines, tetrahydrofuran, nitrobenzene, nitrotoluene, glymes (e.g., glyme, diglyme and tetraglyme), and the like, and their combinations. Organic-based solvents that have 1 to about 8 carbon atoms per molecule are preferred.

A wide variety of complexing or solubilizing agents may be employed to solubilize silver to the desired concentration in the impregnating medium. Useful complexing or solubilizing agents include amines, ammonia, lactic acid and combinations thereof. For example, the amine can be an alkylene diamine having from 1 to 5 carbon atoms. In a preferred embodiment, the solution comprises an aqueous solution of silver oxalate and ethylene diamine. The complexing/solubilizing agent may be present in the impregnating solution in an amount from about 0.1 to about 5.0 moles of ethylene diamine per mole of silver, preferably from about 0.2 to about 4.0 moles, and more preferably from about 0.3 to about 3.0 moles of ethylene diamine for each mole of silver.

The concentration of silver salt in the silver impregnation solution is typically in the range from about 0.1% by weight to the maximum permitted by the solubility of the particular silver salt in the solubilizing agent employed. More typically, the concentration of silver salt is from about 0.5% to 45% by weight of silver, and even more typically, from about 5 to 35% by weight.

Any one or more promoting species can also be included in the silver impregnation solution in order to deposit one or more promoting species, as described above, into the carrier along with the silver. In some embodiments, the one or more promoters are selected from Cs, Li, W, F, P, Ga, Re, and S.

After impregnation with silver and any promoters, the impregnated carrier is removed from the solution and calcined for a time sufficient to reduce the silver component to metallic silver and to remove volatile decomposition products from the silver-containing support. The calcination is typically accomplished by heating the impregnated carrier, preferably at a gradual rate, to a temperature in a range of about 200° C. to about 600° C., more typically from about 200° C. to about 500° C., more typically from about 250° C. to about 500° C., and more typically from about 200° C. or 300° C. to about 450° C., at a reaction pressure in a range from about 0.5 to about 35 bar. In general, the higher the temperature, the shorter the required calcination period. A wide range of heating periods have been described in the art for the thermal treatment of impregnated supports. Reference is made, for example, to U.S. Pat. No. 3,563,914, which indicates heating for less than 300 seconds, and U.S. Pat. No. 3,702,259, which discloses heating from 2 to 8 hours at a temperature of from 100° C. to 375° C. to reduce the silver salt in the catalyst. A continuous or step-wise heating program may be used for this purpose. During calcination, the impregnated support is typically exposed to a gas atmosphere comprising an inert gas, such as nitrogen. The inert gas may also include a reducing agent.

After calcining the catalyst, the calcined catalyst is typically loaded into reactor tubes of an epoxidation reactor, typically a fixed bed tubular reactor, utilizing conventional loading methods well known to those skilled in the art. After loading, the catalyst bed may be swept by passing an inert gas, such as nitrogen, over the catalyst bed.

The produced catalyst preferably exhibits a selectivity of at least 85% for the conversion of ethylene to ethylene oxide. In different embodiments, the produced catalyst exhibits a selectivity of about or at least, for example, 85%, 86%, 87%, 88%, 89%, 90%, 91%, 92%, or 93%.

In another aspect, the instant disclosure is directed to a method for the vapor phase production of ethylene oxide by conversion of ethylene to ethylene oxide in the presence of oxygen by use of the catalyst described above. Generally, the ethylene oxide production process is conducted by continuously contacting an oxygen-containing gas with ethylene in the presence of the catalyst at a temperature in the range from about 180° C. to about 330° C., more typically from about 200° C. to about 325° C., and more typically from about 225° C. to about 270° C., at a pressure which may vary from about atmospheric pressure to about 30 atmospheres depending on the mass velocity and productivity desired. Pressures in the range of from about atmospheric to about 500 psi are generally employed. Higher pressures may, however, be employed within the scope of the invention. Residence times in large-scale reactors are generally on the order of about 0.1 to about 5 seconds. A typical process for the oxidation of ethylene to ethylene oxide comprises the vapor phase oxidation of ethylene with molecular oxygen in the presence of the inventive catalyst in a fixed bed, tubular reactor. Conventional commercial fixed bed ethylene oxide reactors are typically in the form of a plurality of parallel elongated tubes (in a suitable shell). In one embodiment, the tubes are approximately 0.7 to 2.7 inches O.D. and 0.5 to 2.5 inches I.D. and 15-45 feet long filled with catalyst.

The inventive catalysts have been shown to be particularly selective catalysts in the oxidation of ethylene with molecular oxygen to ethylene oxide. The conditions for carrying out such an oxidation reaction in the presence of the catalyst of the present invention may broadly include those known in the art. This applies, for example, to suitable temperatures, pressures, residence times, diluent materials (e.g., nitrogen, carbon dioxide, steam, argon, methane or other saturated hydrocarbons), the presence or absence of moderating agents to control the catalytic action (e.g., an organochloride, such as 1, 2-dichloroethane, vinyl chloride or ethyl chloride), the desirability of employing recycle operations or applying successive conversion in different reactors to increase the yields of ethylene oxide, and other particular conditions that may be beneficial for converting ethylene to ethylene oxide. Molecular oxygen employed as a reactant may be obtained from conventional sources, and may be relatively pure oxygen, or a concentrated oxygen stream comprising oxygen in a major amount with lesser amounts of one or more diluents such as nitrogen or argon, or air.

In the production of ethylene oxide, reactant feed mixtures typically contain from about 0.5 to about 45% ethylene and from about 3 to about 15% oxygen, with the balance comprising comparatively inert materials including such substances as nitrogen, carbon dioxide, methane, ethane, argon and the like. Only a portion of the ethylene is typically reacted per pass over the catalyst. After separation of the desired ethylene oxide product and removal of an appropriate purge stream and carbon dioxide to prevent uncontrolled build up of inert products and/or by-products, unreacted materials are typically returned to the oxidation reactor. For purposes of illustration only, the following are conditions that may be used in a conventional industrial ethylene oxide reactor units: a gas hourly space velocity (GHSV) of 1500-10,000 $h^{-1}$, a reactor inlet pressure of 150-400 psig, a coolant temperature of 180-315° C., an oxygen conversion level of 10-60%, and an EO production (work rate) of 100-300 kg EO per cubic meters of catalyst per hour. Typically, the feed composition at the reactor inlet comprises 1-40% ethylene, 3-12% oxygen, 0.3-40% $CO_2$, 0-3% ethane, 0.3-20 ppmv total concentration of organic chloride moderator, with the balance of the feed being argon, methane, nitrogen, or a mixture thereof.

In some embodiments, the ethylene oxide production process includes the addition of oxidizing gases to the feed to increase the efficiency of the process. For example, U.S. Pat. No. 5,112,795 discloses the addition of 5 ppm of nitric oxide to a gas feed having the following general composition: 8 volume % oxygen, 30 volume % ethylene, about 5 ppm ethyl chloride, and the balance nitrogen.

The resulting ethylene oxide is separated and recovered from the reaction products using methods known in the art. The ethylene oxide process may include a gas recycle process wherein a portion or substantially all of the reactor effluent is re-admitted to the reactor inlet after substantially or partially removing the ethylene oxide product and any byproducts. In the recycle mode, carbon dioxide concentrations in the gas inlet to the reactor may be, for example, from about 0.3 to about 6 volume percent.

Examples have been set forth below for the purpose of further illustrating the invention. The scope of this invention is not to be in any way limited by the examples set forth herein.

EXAMPLES

Carriers A, B, C, D and E were prepared at the typical conditions known to the skilled person for obtaining the water absorption, surface area and carrier sintering heat loads values as shown in Table 1. The water absorption values set forth in Tables 1 and 4 were determined as a percentage of the mass of the carrier in accordance with Japanese Standard Association HS R2205). Further, the surface area specified in Tables 1 and 4 is the BET specific surface area. The carrier sintering heat load was obtained by installing a Referthermo™ temperature measuring sensor in a furnace, sintering the Referthermo™ temperature measuring sensor with the carrier, measuring a dimension of the Referthermo™ temperature measuring sensor after sintering with calipers, and reading an instruction temperature corresponding to the measured dimension from a comparison table, available from the manufacturer of the Referthermo™ temperature measuring sensor. The same technique using the Referthermo™ temperature measuring sensor was used to the carriers' sintering heat load reported in Table 4. Besides the use of the Referthermo™ temperature measuring sensor, other techniques of measuring firing conditions and heat "work" or "load" are also suitable, including conventional temperature measurement equipment such as an optical pyrometer or thermocouple, or pyrometric cones such as Seger cones and Orton cones In carriers A, B, C, D and E, $SiO_2$ from addition of a silicon-containing binder and from the alumina impurity were varied as shown in Table 2. Carriers "A" and "B" are within the scope of the present invention—having less than 0.6 wt % inorganic binder species, in this case $SiO_2$.

Here, carriers A, B, C, D and E shown in Table 1 and Table 2 were manufactured in the following manner (also applied to carriers A1-A4 shown in Tables 4 and 5). First, an alumina mixture was manufactured by mixing an alumina (granule of a low soda alumina) of a primary particle size 2 μm and a silica sol of an average particle size 500 nm at following ratios.

Alumina mixture for carrier A: alumina 100 parts, silica sol 0 parts

Alumina mixture for carrier B: alumina 99.7 parts, silica sol 0.3 parts

Alumina mixture for carrier C: alum a 99.4 parts, silica sol 0.6 parts

Alumina mixture for carrier D: alumina 99.2 parts, silica sol 0.8 parts

Alumina mixture for carrier E: alumina 98.0 parts, silica sol 2.0 parts

Alumina mixtures for carrier A1-A4 shown in Tables 4 and 5 are the same as the alumina mixture for carrier A.

Then, a kneaded mixture was manufactured by adding methyl cellulose 6 parts, water-insoluble cellulose 3 parts, wax emulsion 10 parts and water 30 parts as a molding aid and a binder to the alumina mixture 100 parts, and kneading the alumina mixture obtained by adding in a kneading machine.

Then, a tubular molded body with outer diameter 8 mm, inner diameter 3 mm and length 8 mm was manufactured by extruding the kneaded mixture.

Then, a dried body was manufactured by drying the tubular molded body for one hour at 60° C.~200° C.

Finally, carriers A, B, C, D and E (same applied to carrier A1-A4 shown in Tables 4 and 5) were manufactured by filling a dried body in a firing vessel, and putting the firing vessel in a firing furnace, and firing the dried body for 1 hour at carrier sintering heat load (temperature) shown in Table 1.

Ethylene epoxidation catalysts were then prepared using these carriers. First, a silver solution was prepared from the following components (by weight):

Silver oxide—800 parts
Oxalic acid—426.5 parts
Ethylene diamine—543.6 parts
Deionized water—695.5 parts Deionized water was placed in a cooling bath to maintain temperature during the whole preparation under 45° C. At continuous stirring, ethylenediamine was added in small portions. Oxalic acid dihydrate was then added to the water-ethylenediamine solution in small portions. After all oxalic acid was dissolved, high purity silver oxide was added to solution in small portions. After all silver oxide was dissolved and the solution was cooled to about 35° C. it was removed from the cooling bath and filtered. After filtration, the solution contained roughly 30 wt % silver, and had a specific gravity of 1.55 g/mL.

While thoroughly mixing the silver solution, promoters were added to the solution in catalytically active amounts individually or as a mixture of aqueous based solutions. It may be used for example, Cs as CsOH, Li as $LiNO_3$, Re as $HReO_4$, W as ammonium metatungstate, and S as $(NEL_1)_2SO_4$ for promoters. The specific promoter content was optimized to provide maximum stability at high selectivity as understood by the skilled person. High selectivity was achieved by maintaining concentrations of Cs in the range of 400 ppm to 1000 ppm, Li in the range 100-200 ppm, Re in the range 200-400 ppm, W in the range 50-200 ppm, and S in the range 20-100 ppm on the catalyst. Based on the amount of silver oxide added to the silver solution as set forth above, the catalyst comprised silver at a nominal 16.5 wt %.

Then a flask containing a 100 g to 300 g sample of one of the carriers, above, was evacuated until the pressure was below 20 mm Hg. Then 200-300 mL of the silver/promoter solution to cover the carrier was introduced to the flask under vacuum. The vacuum was released after about 5 minutes to restore ambient pressure, hastening complete penetration of the solution into the pores. Subsequently, the excess impregnation solution was drained from the impregnated carrier to produce the finished catalyst.

The selectivity and activity data of the catalyst were obtained by using catalyst testing procedures well-known to the skilled person. The catalyst samples were crushed, ground and screened to provide a sample of 14-18 mesh particles. 10.5 grams of the material were then charged into ¼" outer diameter heated microreactors with adjustable feed (ethylene, oxygen and $CO_2$) and chloride concentrations control. The catalysts were first conditioned under an atmosphere of 8% ethylene, 4% oxygen, 4% carbon dioxide, and 2 ppm chlorides at a temperature of 255° C. for 60-70 hours after which the feed composition was changed to 30% ethylene, 7% oxygen, 1% carbon dioxide, and 1 ppm chlorides with the temperature being lowered to 230° C. The temperature was automatically raised to reach testing conditions at ΔEO of 3.8 mol %, and at a work rate of 355 kg EO/kg cat/h. The chloride concentrations were adjusted during the test to maintain maximum selectivity at lowest possible temperature of reaction.

Table 3 shows the results of the catalyst testing. Specifically, lowering Si in the carrier formulation and increasing the carrier sintering heat load improves maximum selectivity and selectivity and activity stability. Here, $S_{SOR}$ is a selectivity at the time of catalyst evaluation start of run (same applies for $S_{SOR}$ in Table 5). $S_{500\ hr}$ is a selectivity at the time of 500 hours from the catalyst evaluation start of run. $S_{1000\ hr}$ is a selectivity at the time of 1000 hours from the catalyst evaluation start of run. $T_{SOR}$ is the reaction temperature at the time of catalyst evaluation start of run. $T_{500}$ is a reaction temperature at the time of 500 hours from the catalyst evaluation start of run. $T_{10000\ hr}$ is a reaction temperature at the time of 1000 hours from the catalyst evaluation start of run. The catalyst active layer supported on the surface of the carriers A, B, C, D and E is silver.

As mentioned above, Carrier A was prepared according to the present invention and thus to be substantially free of inorganic binders. Carriers A1, A2, A3, A4 were prepared at the typical conditions known to the skilled person to obtain the water absorption, surface area and carrier sintering heat loads values as shown in Table 4 (Carrier A is also included in Table 4 for comparison). Additionally, like Carrier A, carriers A1, A2, A3, and A4 were also prepared to be substantially free of inorganic binder species, more specifically, carriers A1, A2, A3, and A4 contain no inorganic binder species.

Table 5 shows that the carrier sintering load should be higher than 1530° C. for maximum selectivity.

TABLE 1

Properties of Surface Area and Water Absorption, and Carrier sintering heat load of carriers with $SiO_2$ in formulation.

| Physical properties | | Carrier | | | | |
| --- | --- | --- | --- | --- | --- | --- |
| | | A | B | C | D | E |
| Surface Area | m²/g | 0.66 | 0.65 | 0.64 | 0.65 | 0.61 |
| Water Absorption | % | 44.5 | 43.4 | 44.9 | 45.2 | 46.6 |
| Carrier sintering heat load | °C. | 1531 | 1527 | 1527 | 1501 | 1468 |

TABLE 2

$SiO_2$ content rate in carrier after measuring Si content rate by inductively coupled plasma (ICP) emission spectrophotometer, converting from the Si content rate to $SiO_2$ content rate)

| containing | | Carrier | | | | |
| --- | --- | --- | --- | --- | --- | --- |
| component | | A | B | C | D | E |
| $SiO_2$ | % | 0.075 | 0.357 | 0.628 | 0.963 | 2.172 |

TABLE 3

Selectivity and activity Start of Run and stability for catalysts made on carriers.

| Carrier | $S_{SOR}$ % | $S_{500hr}$ % | $S_{1000hr}$ % | $T_{SOR}$ °C. | $T_{500hr}$ °C. | $T_{1000hr}$ °C. |
| --- | --- | --- | --- | --- | --- | --- |
| A | 89.6 | 89.5 | 89.5 | 243 | 246 | 249 |
| B | 89.4 | 88.6 | 88.4 | 247 | 250 | 249 |
| C | 89.2 | 86.2 | na | 247 | 246 | na |
| D | 89.2 | 82.0 | na | 241 | 250.0 | na |
| E | 87.9 | <80 | na | 235 | >260 | na |

TABLE 4

Surface Area and Water Absorption properties of carrier A preparations with varying heat load.

| Physical properties | | Carrier | | | | |
| --- | --- | --- | --- | --- | --- | --- |
| | | A1 | A2 | A | A3 | A4 |
| Surface Area | m²/g | 0.70 | 0.65 | 0.66 | 0.63 | 0.59 |
| Water absorption | % | 43.8 | 45.7 | 44.5 | 43.6 | 43.7 |
| Carrier sintering heat load | °C. | 1475 | 1518 | 1531 | 1555 | 1569 |

TABLE 5

Selectivity of at the time of catalyst evaluation start of run of catalysts on carrier A after different heat loads.

| Carrier | $S_{SOR}$ % | $T_{SOR}$ °C. |
| --- | --- | --- |
| A1 | 87.5 | 245 |
| A2 | 88.4 | 250 |
| A | 89.5 | 246 |
| A3 | 89.5 | 249 |
| A4 | 89.2 | 247 |

In all aspects within the framework of the present disclosure, various disclosed elements (including each element of each claim, each element of the embodiments and examples, each element of each drawing and the like) can be combined variously and selected.

While there have been shown and described what are presently believed to be the preferred embodiments of the present invention, those skilled in the art will realize that other and further embodiments can be made without departing from the spirit and scope of the invention described in this application, and this application includes all such modifications that are within the intended scope of the claims set forth herein.

What is claimed is:

1. A method for producing a carrier for an ethylene epoxidation catalyst in which the carrier comprises a porous alumina body formed of sintered particles of low soda alumina in a substantial absence of inorganic oxides other than alumina, the method comprising:
   a) preparing a composition comprising low soda alumina particles, water, and a volatile organic binder, in the substantial absence of inorganic oxides other than alumina;
   b) molding the composition into a structure;
   c) heating the structure to volatilize the volatile organic binder and form a porous structure; and
   d) sintering the porous structure at a temperature of 1350° C. or above to produce the porous alumina body formed of sintered particles of low soda alumina in a substantial absence of inorganic oxides other than alumina;
   wherein the substantial absence of inorganic oxides corresponds to an amount of no more than 0.5 wt % inorganic oxides other than alumina and comprises at least a substantial absence of silicon-containing species.

2. The method of claim 1, wherein the substantial absence of inorganic oxides corresponds to an amount of less than 0.1 wt % inorganic oxides other than alumina.

3. The method of claim 1, wherein the substantial absence of inorganic oxides corresponds to an amount of 0.05 wt % or less inorganic oxides other than alumina.

4. The method of claim 1, wherein the low soda alumina particles have an α-alumina composition in a substantial absence of other types of alumina.

5. The method of claim 1, wherein the silicon-containing species are in an amount of less than 0.5 wt %.

6. The method of claim 1, wherein, in the sintering, a sintering temperature is 1500° C. or more and 1650° C. or less.

7. The method of claim 1, wherein in the sintering, a sintering time is 10 minutes or more and 10 hours or less.

8. The method of claim 1, wherein the carrier has a B.E.T. surface area in a range of about 0.1 to 10 m²/g.

9. The method of claim 1, wherein a pore size of 1-10 μm of the carrier contributes at least 50% of a total pore volume of the carrier, and a pore size of 5-10 μm of the carrier contributes at most 25% of the total pore volume of the carrier.

* * * * *